(12) United States Patent
Nelson et al.

(10) Patent No.: US 6,682,501 B1
(45) Date of Patent: *Jan. 27, 2004

(54) SUBMUCOSAL TONSILLECTOMY APPARATUS AND METHOD

(75) Inventors: Lionel Nelson, Los Altos Hills, CA (US); Stuart D. Edwards, Portola Valley, CA (US); Ashoor Shahbazi Yourgenlow, San Jose, CA (US)

(73) Assignee: Gyrus ENT, L.L.C., Bartlett, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/329,717

(22) Filed: Jun. 10, 1999

Related U.S. Application Data

(63) Continuation-in-part of application No. 08/905,991, filed on Aug. 5, 1997, now Pat. No. 5,843,021, which is a continuation-in-part of application No. 08/642,327, filed on May 3, 1996, now Pat. No. 5,807,308, which is a continuation-in-part of application No. 08/606,195, filed on Feb. 23, 1996, now Pat. No. 5,707,349.

(51) Int. Cl.[7] .......................... A61B 17/20; A61B 18/18
(52) U.S. Cl. .......................................... 604/22; 606/41
(58) Field of Search .............. 604/22, 21; 606/22–34, 606/37–42, 45–52, 110, 111; 602/96–102, 134, 135, 154, 156

(56) References Cited

U.S. PATENT DOCUMENTS

| | | | |
|---|---|---|---|
| 4,011,872 A | 3/1977 | Komiya | 128/303.14 |
| 4,074,718 A * | 2/1978 | Morrison, Jr. | 128/303.14 |
| 4,411,266 A | 10/1983 | Cosman | 128/303.18 |
| 4,532,924 A | 8/1985 | Auth et al. | 128/303.17 |
| 4,565,200 A | 1/1986 | Cosman | 128/642 |
| 4,907,589 A | 3/1990 | Cosman | 606/34 |
| 4,947,842 A | 8/1990 | Marchosky et al. | 128/401 |
| 4,966,597 A | 10/1990 | Cosman | 606/50 |
| 4,976,711 A | 12/1990 | Parins et al. | 606/48 |
| 5,057,107 A | 10/1991 | Parins et al. | 606/48 |
| 5,078,717 A | 1/1992 | Parins et al. | 606/48 |
| 5,083,565 A | 1/1992 | Parins | 128/642 |
| 5,100,423 A | 3/1992 | Fearnot | 606/159 |
| 5,122,137 A | 6/1992 | Lennox | 606/40 |
| 5,125,928 A | 6/1992 | Parins et al. | 606/48 |
| 5,190,541 A | 3/1993 | Abele et al. | 606/46 |
| 5,197,963 A | 3/1993 | Parins | 606/46 |
| 5,197,964 A | 3/1993 | Parins | 606/48 |
| 5,215,103 A | 6/1993 | Desai | 128/784 |
| 5,257,451 A | 11/1993 | Edwards et al. | 29/825 |
| 5,681,276 A * | 10/1997 | Lundquist | 604/22 |
| 5,707,349 A | 1/1998 | Edwards | 604/22 |
| 5,718,702 A | 2/1998 | Edwards | 606/41 |
| 5,743,904 A | 4/1998 | Edwards | 606/32 |
| 5,836,906 A * | 11/1998 | Edwards | 604/22 |
| 5,863,290 A * | 1/1999 | Gough et al. | 606/1 |
| 6,030,383 A * | 2/2000 | Benderev | 606/45 |
| 6,106,521 A * | 8/2000 | Blewett et al. | 606/41 |
| 6,179,803 B1 * | 1/2001 | Edwards et al. | 604/22 |
| 6,334,068 B1 * | 12/2001 | Hacker | 600/545 |

FOREIGN PATENT DOCUMENTS

| | | | |
|---|---|---|---|
| WO | WO 92/10142 | 6/1992 | |
| WO | WO 96/29946 | 10/1996 | |
| WO | WO 99/07299 | 2/1999 | ........... A61B/17/39 |

* cited by examiner

*Primary Examiner*—Manuel Mendez
(74) *Attorney, Agent, or Firm*—Heller Ehrman White & McAuliffe (57) ABSTRACT

A cell necrosis apparatus includes an elongated member with a longitudinal axis. The elongated member being is configured to be positionable and maneuverable in an oral cavity. First and second energy delivery devices are positioned at a distal portion of the elongated member. Each of the first and second energy delivery devices is laterally offset from the longitudinal axis. In another embodiment, the apparatus can also include a template with a tissue penetrating introducer and a lumen. The energy delivery device is configured to be advancable from the first lumen into a tonsil intratonsil lymphoid stroma.

22 Claims, 11 Drawing Sheets

SUBMUCOSAL TONSILLECTOMY APPARATUS AND METHOD

CROSS-REFERENCE TO RELATED APPLICATIONS

This application is a continuation of U.S. patent application Ser. No. 08/905,991, filed Aug. 5, 1997, entitled "Cell Necrosis Apparatus", which is a continuation-in-part of U.S. patent application Ser. No. 08/642,327, filed May 3, 1996, entitled "Method for Treatment of Airway Obstructions", which application is a continuation-in-part application of U.S. patent application Ser. No. 08/606,195, filed Feb. 23, 1996, entitled "Method for Treatment of Airway Obstructions", which cross-references U.S. patent application Ser. No. 08/516,781 filed Aug. 18, 1995, entitled "Ablation Apparatus and System for Removal of Soft Palate Tissue", having named inventors Stuart D. Edwards, Edward J. Gough and David L. Douglass, which is a continuation-in-part of U.S. application Ser. No. 08/239,658, filed May 9, 1994 entitled "Method for Reducing Snoring by RF Ablation of the Uvula" This application is also related to an application Ser. No. 08/642,053, filed May 3, 1996, entitled "Method and Apparatus for Treatment of Air Way Obstructions", all incorporated by reference herein.

BACKGROUND OF THE INVENTION

1. Field of the Invention

This invention relates to an apparatus to treat tonsils, and more particularly, to an apparatus that creates cell necrosis within the intratonsil lymphoid stroma while substantially preserving the underlying tonsil capsule and overlying mucosa.

2. Description of Related Art

Tonsillectomy is a procedure indicated for recurrent infection of the tonsils and surrounding tissues and/or airway obstruction caused by the tonsils. It is one of the most frequently performed operations in the western world. Post-operatively, it is also one of the most painful due to the resultant exposure of unprotected oropharyngeal nerve and surrounding muscle tissue. The healing process is a slow taking between two to three weeks for the injured tissue to become overgrown with new epithelial/mucous membrane tissue. This period is typically characterized by considerable pain, dehydration and weight loss due to difficulty in swallowing as well as occasional hemorrhaging.

Tonsillectomies and adenotonsillectomies are some of the most commonly performed surgical procedures in the United States and elsewhere, with an estimated 340,000 procedures performed in the United States each year. The major complication of tonsillectomy is post-operative hemorrhage. With refinements tonsils techniques are removed over time have been refined, electrocoagulation has been used more frequently to achieve hemostasis.

While suction electrocoagulation for removal of tonsils is an effective method with minimal blood loss (e.g. blood vessels are electrocoagulated as they are encountered), the procedure has several important limitations. First is the fact that coagulation causes trauma to surrounding and subjacent tissues 1 to 2 mm beyond the point of contact. This causes unwanted tissue necrosis and may lead to late post-operative bleeding. Also, suction electrocoagulation devices heretofore presented are not good dissecting instruments. Nonetheless, there is a tendency to use such electrocoagulation devices to cut through adherent tissue which leads to even greater tissue trauma. The other option is to switch back and forth between using a suction electrocoagulation device and a dissecting instrument such as a Fischer "hockey-stick" style dissector. Such switching between instruments prolongs the surgery and the time the patient must remain under anesthetic, permits additional hemorrhaging during instrument changes, and decreases efficiency.

Another method for the removal of tonsils involves the use of bipolar electrocoagulating forceps. With bipolar electrocoagulation, tissue damage is limited to the tissue between the tines of the bipolar coagulator. A recent study by Dr. Mario Andrea in the October, 1993 edition of Laryngoscope used this technique in 265 patients. The study demonstrated its effectiveness and also negligible delayed post-operative bleeding. The bipolar electrocoagulating forceps is designed principally for coagulation. If suction is needed, which is not uncommon, another instrument must be introduced into the operating field. To some degree, a bipolar coagulator may be used as a dissecting instrument; there are many instances where conventional dissection is more advantageous as dissection is not inherent in the bipolar coagulator's design.

There is a need for an apparatus to treat the tonsil and perform a tonsillectomy with minimal bleeding. There is a further need for an apparatus to treat the tonsils and perform a tonsillectomy without total removal of the tonsils. Yet a further need exists for an apparatus to perform a tonsillectomy by ablating the intratonsil lymphoid stroma. Still a further need exists for an apparatus to treat tonsillectomy by ablating the intratonsil lymphoid stroma while preserving the tonsil's underlying fibrous capsule and overlying mucosa.

SUMMARY OF THE INVENTION

Accordingly, an object of the invention is to provide an apparatus to treat tonsils.

Another object of the invention is to provide an apparatus to create controlled necrosis within a tonsil, particularly the intratonsil lymphoid stroma.

A further object of the invention is to provide an apparatus to create controlled necrosis of the intratonsil lymphoid stroma while substantially preserving the tonsil's underlying fibrous capsule and overlying mucosa.

Yet another object of the invention is to provide a method to create controlled cell necrosis of a tonsil's intratonsil lymphoid stroma.

Still another object of the invention is to provide a method to create controlled cell necrosis of the tonsil's intratonsil lymphoid stroma while substantially preserving the underlying fibrous capsule and overlying mucosa.

These and other objects of the invention are achieved in a cell necrosis apparatus. The apparatus includes an elongated member with a longitudinal axis. The elongated member being is configured to be position able and maneuverable in an oral cavity. First and second energy delivery devices are positioned at a distal portion of the elongated member. Each of the first and second energy delivery devices is laterally offset from the longitudinal axis.

In another embodiment, the tonsil treatment apparatus includes a template including a first tissue penetrating introducer with a first lumen. A first energy delivery device is at least partially position able in the first lumen. The first energy delivery device is advancable from the first lumen into a tonsil intratonsil lymphoid stroma.

In yet another embodiment, a method of reducing the size of the tonsil provides an elongated member coupled to a first energy delivery device with an energy delivery surface. At least a portion of the energy delivery surface is delivered into an interior of the tonsil. Cell necrosis is created in the tonsil intratonsil lymphoid stroma while preserving a tonsil fibrous capsule.

DETAILED DESCRIPTION

Figure 1:
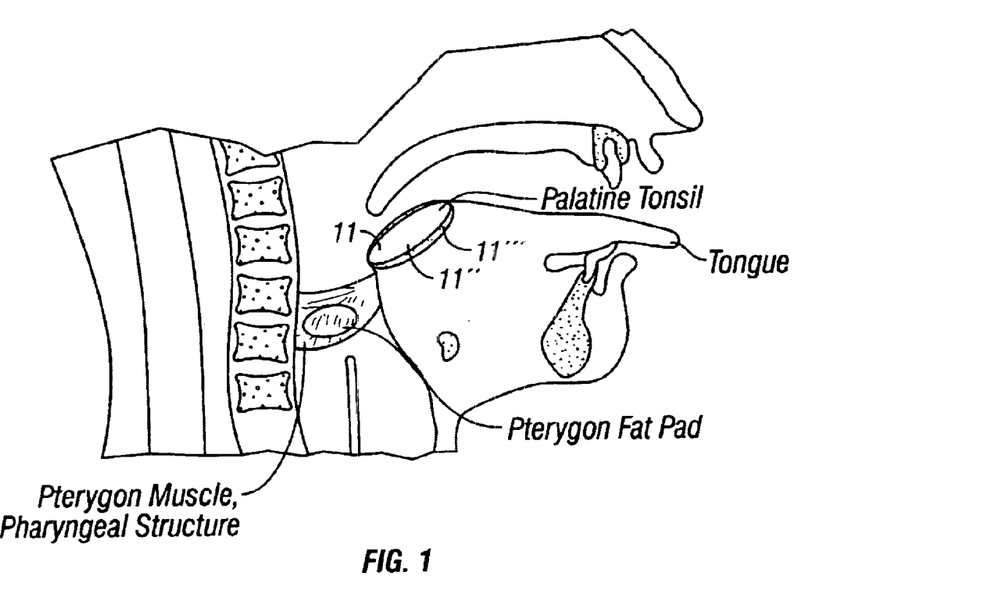
FIG. 1 is a lateral view of the oral cavity illustrating the anatomy of the oral cavity including the tonsil and pterygoid muscle and fat pad.
Figure 2A:
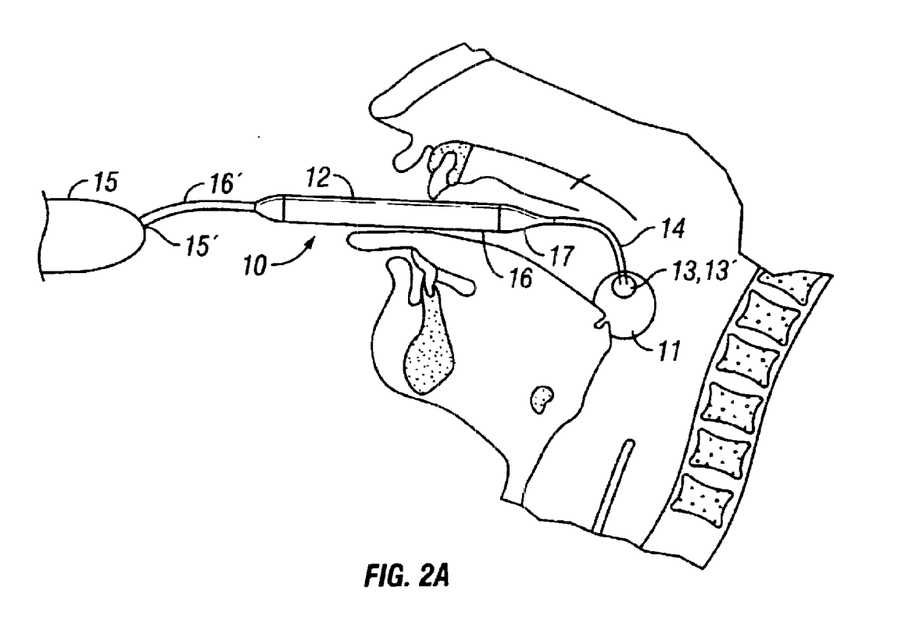
FIG. 2a is a lateral view of the oral cavity illustrating positioning of the tonsil treatment apparatus of the present invention in the oral cavity and tonsil treatment site.
Figure 2B:
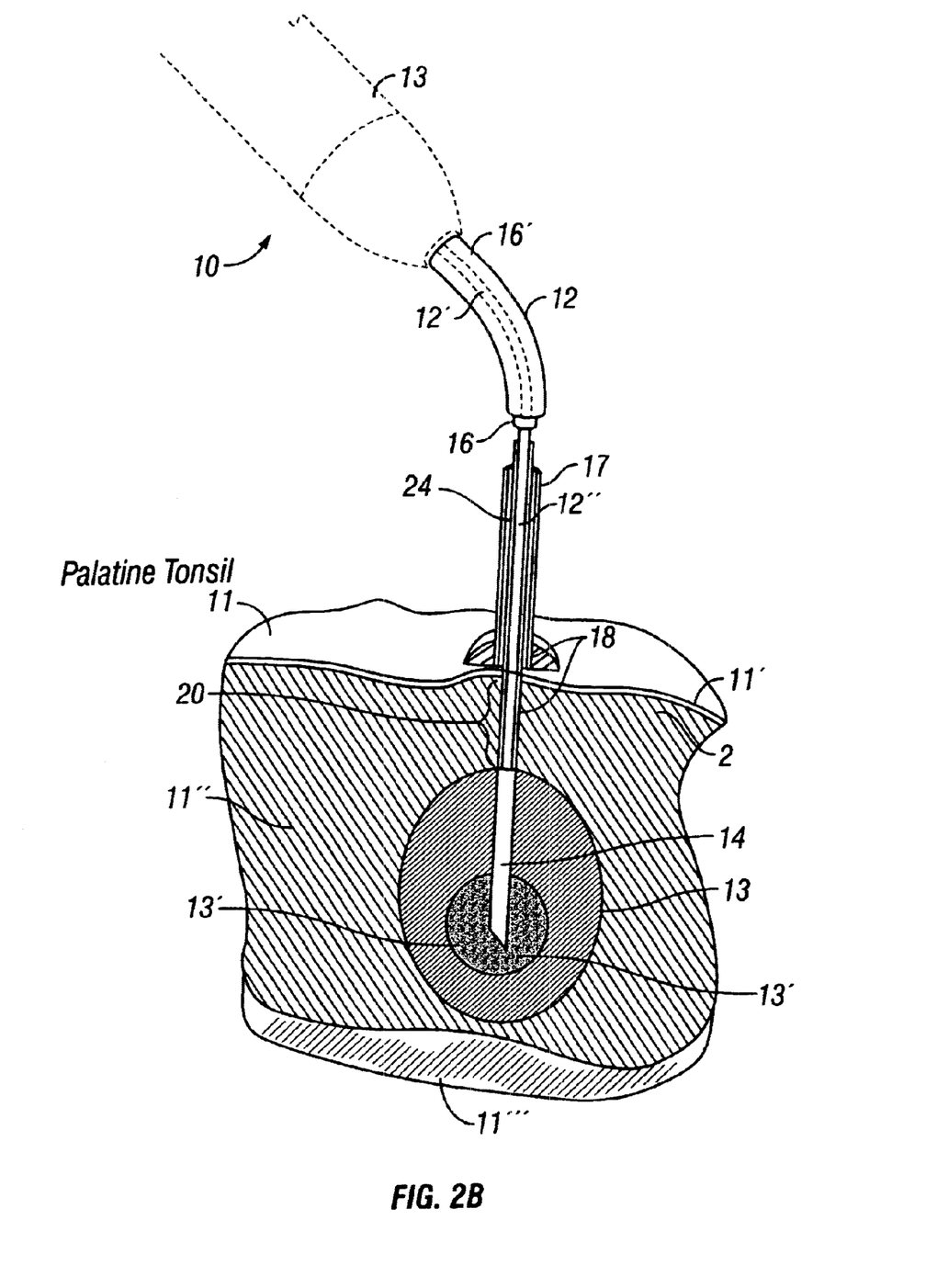
FIG. 2b is a perspective view illustrating positioning of the tonsil treatment apparatus and the creation of cell necrosis of the stroma of the tonsil.

Referring now to FIGS. 1–2, one embodiment of a cell necrosis apparatus 10 (also called tonsil treatment apparatus 10 and submucosal tonsillectomy apparatus 10) used to treat tonsil 11 delivers energy to a treatment site 13 in the tonsil such as the intratonsil lymphoid stroma 11" (or other tonsil layer or oral structure) to create an area 13' of controlled cell necrosis an/or ablation while substantially preserving or minimizing injury to a tonsilar mucosal surface 11' and tonsil fibrous capsule 11"'. For purposes of this disclosure, an ablation procedure shall be meant to include one or more of the following affects: thermal damage, tissue shrinkage, tissue scarring, remodeling, debulking and ablating tissue. The necrosed or ablated area 13' results in a subsequent reduction in volume of tonsil 11 particularly at or around ablated area 13'. It will be appreciated that the apparatus of the present invention is equally applicable or can otherwise be configured to treat the lingual tonsils, soft palate, turbinates, uvula, pharyngeal structures and the like. In one embodiment apparatus 10 can be configured to treat the pterygoid fat pad or other pharyngeal structures.

Cell necrosis apparatus 10 can be positioned at a treatment site 13 to deploy one or more energy delivery devices 14, also called electrodes 14. Each energy delivery device 14 may be a needle energy delivery device and each is introduced into an interior of the tonsil 11 through a surface 11' of the tonsil. Ablation apparatus 10 may include traumatic intubation with or without visualization, provide for the delivery of oxygen or anesthetics, and can be capable of suctioning blood or other secretions.

Referring now to FIGS. 2a–2b, in one embodiment, apparatus 10 is used to treat the tonsils 11. Specifically, apparatus 10 is used to ablate the intratonsil lymphoid stroma 11" while sparing or minimizing injury to the underlying tonsil capsule 11"' and overlying mucosa 11'. Apparatus 10 is positioned transorally and electrode 14 is advanced through the tonsillar mucosa 11' under local anesthesia. An adequate temperature is attained (e.g. 70 to 100° C.) at the treatment site 13 and/or surrounding tissue in order to sterilize an infected tonsil. In other embodiments apparatus 10 can be configured to treat and ablate selected portions of the pterygoid fat pad (in the pharynx) while substantially preserving and preventing injury to overlying mucosa and underlying muscle and pharyngeal arteries, veins and nerves. Various medical imaging methods known in the art including CT scan, ultrasound, endoscopy and fluoroscopy can used with this procedure to facilitate placement of apparatus 10 in the desired pharnygeal anatomy as well as provide the physician feedback on the ablation process.

Figure 3:
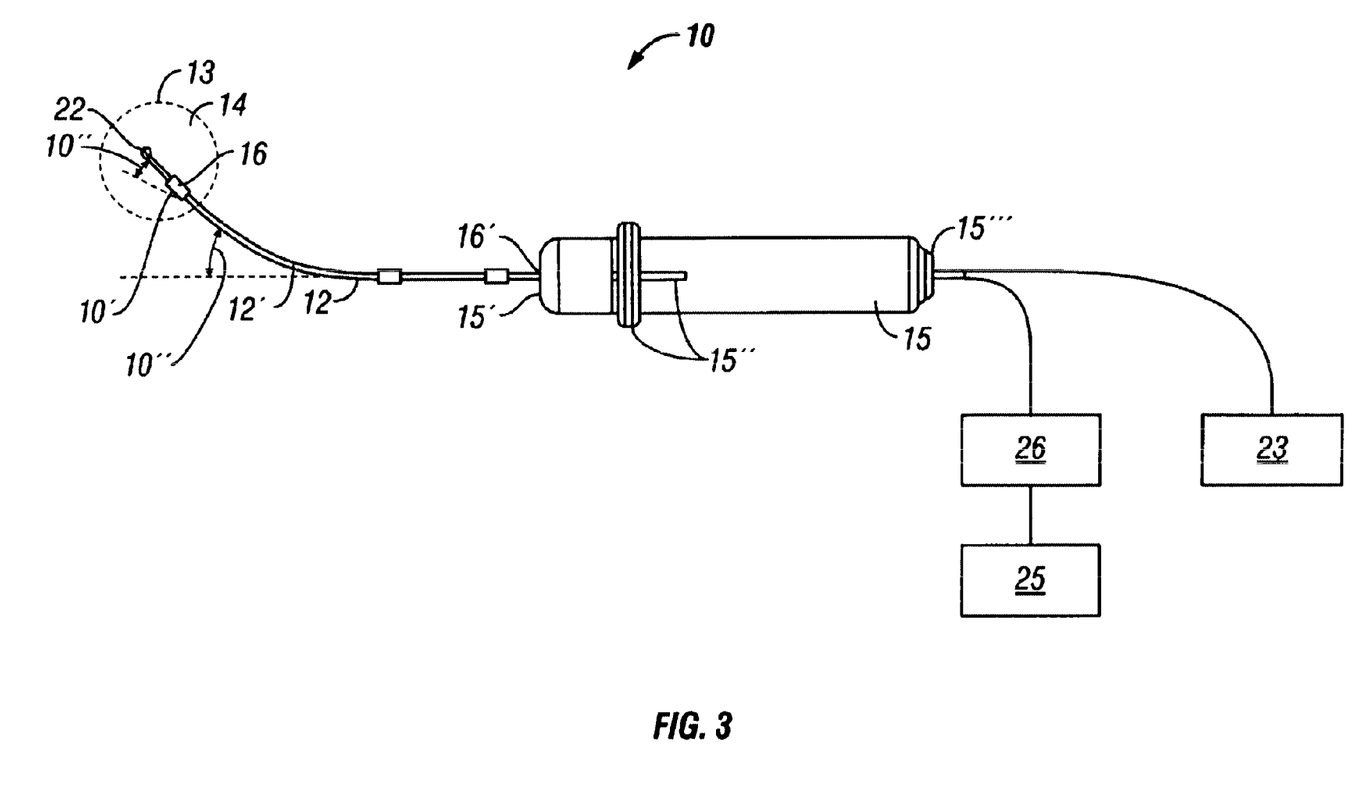
FIG. 3 is a lateral view of the treatment apparatus shown in FIGS. 2a and 2b, illustrating the handpiece, elongated member, template and energy delivery device.
Figure 4:
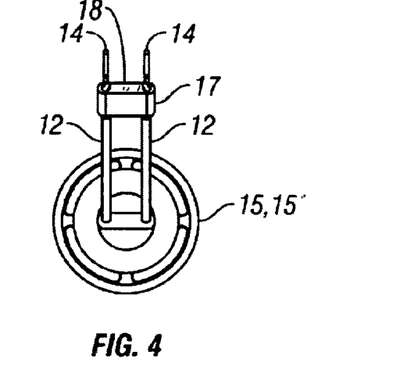
FIG. 4 is a straight-on perspective view of the distal end of the handpiece shown in FIG. 3 illustrating the configuration and connection of the elongated members to the handpiece.
Figure 5:
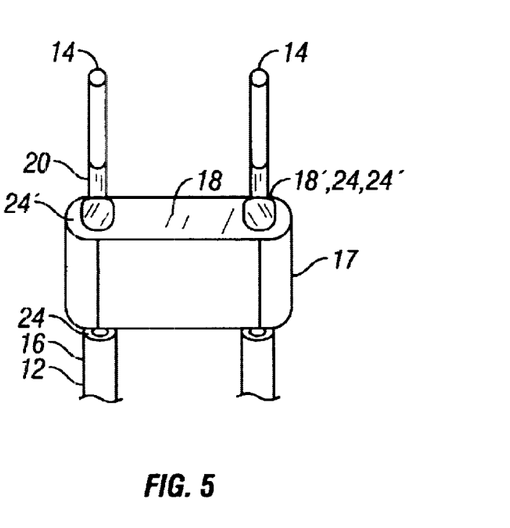
FIG. 5 is closeup view of FIG. 4 illustrating one embodiment of the template and the spacing of the electrodes within the template.

Referring now to FIGS. 2–3, treatment apparatus 10 includes an enlongated member 12 with a longitudinal axis 10'. In one embodiment elongated member 12 is coupled to a handpiece or shell 15. A plurality of energy delivery devices 14 are positioned at a distal portion 16 of elongated member 12. In one embodiment, energy delivery device apparatus 10 is configured to create a selectable area of cell necrosis 13' at treatment site 13.

Elongated member 12 can be a catheter, hypotube, guidewire or handpiece, or a combination thereof that is configured to be both positionable and maneuverable in an oral cavity such as the throat. In various embodiments elongated member 12 can be fabricated from extrudable resilient polymers such as polyethylene, formable metals such as stainless steel, and shape memory metals such as nitinol. In one embodiment elongated member 12 can be a 0.035" nitinol wire which may or may not be coated with an insulating polymer material over all or part of its length. Elongated member can have one or more lumens 12' configured for the advancement of guidewires, catheters, hypotubes, fiberoptic view devices and the like as well as providing ports for providing suction/aspiration, pressure, fluid delivery, and drug delivery. In one embodiment, elongated member 12 can be catheter or hypotube with an advancable corewire 12" such as a 0.035" nitinol wire that is advanced through lumen 12' to reach a target tissue site 13.

In various embodiments, handpiece 15 can be cylindrically shaped and fabricated from moldable plastics such as nylon, polystyrene, polycarbonate, acrylic, or a combination thereof using injection molding or other polymer processing methods known in the art. The distal end 15' of handpiece 15 can be connected to the proximal end 16' of elongated member 12 using adhesive or solvent bonding, hot melt junction, shrink tubing, or other plastic joining method known in the art. In various embodiments handpiece 15 can include a slidable mechanism or actuator 15" which is mechanical coupled to elongated member 12 to laterally advance elongated member 12 within an oral cavity and/or deflect distal portions 16 of elongated member. In one embodiment actuator 15" can comprise a ring that slides over handpiece 15 along a lateral slot within the handpiece. In still other embodiments, handpiece 15 can include an electrical connector 15'" such as a lemo connector used to connect electrode 14 and or sensor 22 to monitoring device 23, control system 25 or a power source 26. In various embodiments one or more elongated members 12 can be coupled to handpiece 15

At least a majority of energy delivery devices 14 are laterally offset from the longitudinal axis 10' by an angle 10". In one embodiment, energy delivery devices 14 are offset by approximately 90 degrees. In other embodiments, energy delivery devices are offset in the range of 0 to 90 degrees with specific embodiments of 15, 30, 45 and 60 degrees. The offset is preferred in order to more readily position energy delivery devices 14 at an exterior 11' of an oral anatomical structure such as tonsil 11.

Referring now to FIGS. 4–7, embodiments of apparatus 10 can also include a template 17 which is positioned at the distal portion 16 of elongated member 12. In one embodiment, template 17 can be a pressure plate that is positioned on an exterior surface of the selected anatomical structure. Template 17 includes a tissue interface surface 18 (illustrated in FIG. 7) which can include all of a portion of the indicated surface depending on the amount of contact between the anatomical structure surface and tissue interface surface 18 which may be dependent on the amount of force applied to the surface of the anatomical structure. In one embodiment tissue interface surface 18 can be configured to be tissue piercing, with a pointed and/or needle shape tip 18' similar to a hypodermic needle.

Template 17 and also be made non-conductive to the transmission of electrical, thermal or other electromagnetic energy. In various embodiments template 17, can be made out of moldable thermoset plastics or forged or machined metals such as stainless steel (304v) or tool steel. In a preferred embodiment shown in FIG. 5, template has two stylets 24 separated by 10 mm (at their center lines) configured to receive and guide two RF electrodes including needle electrodes. In this embodiment, each electrode can be coupled to a separate elongated member 12.

Figure 6:
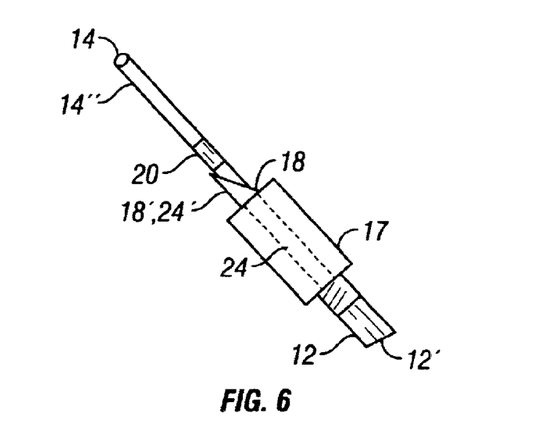
FIG. 6 is an oblique side view of one embodiment of the invention further illustrating the spacing of the distal portion of the elongated member, template, tissue piercing stylets and electrode as well as the use of insulating material over portions of the electrode.
Figure 7:
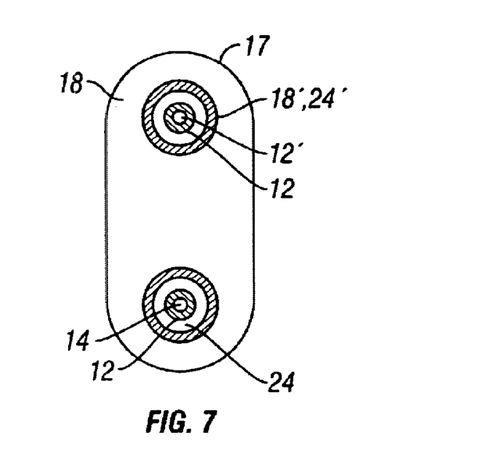
FIG. 7 is a frontal view illustrating the tissue interface surface of the template including lumens/stylet openings.

Referring to FIGS. 6 and 7, in one embodiment, template 17 can have a flat lonzenged shape, while in other embodiments template 17 can be substantially oval, circular or rectangular in shape. Also in various embodiments, template 17 can be configured to have one or more lumens 24 or stylets 24 to hold/guide one or more electrodes 14 into a tonsil tissue site 13. Template 17 can be the size of a tonsil's face, while stylets 24 may be 4 mm hollow channels (or lumens 24) with needle sharp tips 24' which are capable of penetrating mucosal tissue and subjacent fibrous stroma or other tissue.

In one embodiment template 17 includes one or more electrode stylets 24 which extend from tissue interface surface 18. Stylets 24 have tissue-piercing distal ends 24'. The distal ends 14" of electrodes 14 are less tissue piercing than the distal ends 24' of stylets 24 but have geometries that are readily advanceable through tonsil tissue 11 including the intratonsil lymphoid stroma 11" as well as pharyngeal structures such as the pteryguid fat pad. In other embodiments electrode tips 14" are sufficiently tissue piercing to be positioned in tonsil tissue 11 without the use of stylets 24.

Figure 8A:
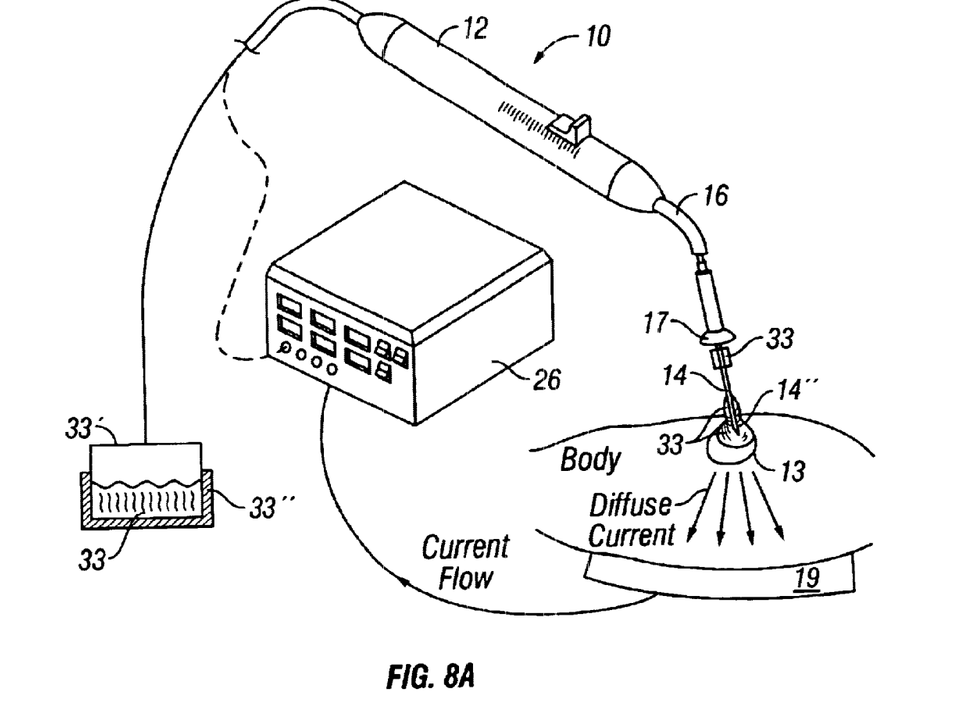
FIG. 8a illustrates a perspective view/schematic diagram of the cell necrosis apparatus of the present invention coupled to an energy source and a ground pad electrode and operation of the electrode in a monopolor mode.
Figure 8B:
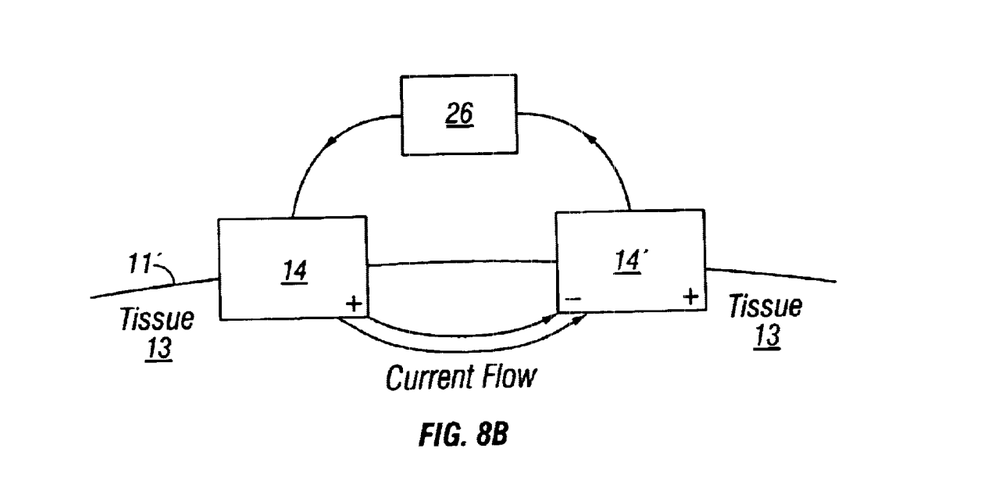
FIG. 8b is a perspective view/schematic diagram illustrating the current flow for RF electrodes operating in a bipolar mode.

In various embodiments, energy delivery device 14 can be an RF electrode, a microwave antenna, ultrasound transducer, resistive heater or liquid thermal jet. Referring now to FIGS. 8a and 8b, in a preferred embodiment, energy delivery device 14 is an is an RF electrode operated in either bipolar or monopolar mode and energy source 26 is an RF source 26. In a monopolar mode of delivering RF energy, a single electrode 14 is used in combination with an indifferent electrode patch 19 electrically coupled to power source 26 that is applied to the body to form the other contact and complete an electrical circuit with power source 26. Bipolar operation is possible when two or more electrodes 14 are used. Current flows from portions of a first electrode 14 to a second electrode 14'. In a preferred embodiment, multiple RF electrodes 14 are included.

RF electrodes 14 are preferably needle electrodes with diameters in the range of 0.005 to 0.5" with specific embodiments of 0.01, 0.05 and 0.1; and including needle gauges of 10–22 with specific embodiments of 12, 18 and 22 gauge. RF electrodes 14 are tissue piercing and advanceable through the selected anatomical structure. Referring back to FIG. 6, an insulator 20 can be positioned at the exterior of one or all of RF electrodes 14. Insulator 20 can be a moveable sleeve. adjustable in length and in a surrounding relationship to an exterior surface of energy delivery device 14. Insulator 20 serves as a barrier to thermal or RF energy flow. Insulator 20 can be in the form of an sleeve that may be adjustably positioned at the exterior of energy delivery device 14. In various embodiment insulator 20 can be made of a polyester shrink wrap (0.002 inch thickness) a polyamide, polyimide or Teflon® material.

Referring to FIGS. 6 and 7a, one or more sensors 22 can be included and positioned at a distal end 14" of electrode 14, at a distal end of insulator 20, as well as at other positions of cell necrosis apparatus 10. Sensor 22 is of conventional design, including but not limited to thermistors, thermocouples, resistive wires, and the like. A suitable sensor 22 is a T type thermocouple with copper constantene, J type, E type, K type, fiber optics, resistive wires, thermocouple IR detectors, and the like.

Each electrode 14 can experience a steep temperature rise or gradient as current moves outward through the electrode. This temperature rise causes tissue that is immediately adjacent to electrode 14 to reach temperatures of 100° C. or more while tissue only 5 to 10 mm away may be at or near body temperature. Because of this temperature gradient, it is often necessary to place and remove electrode 14 several times from the treatment site 13 or use a plurality of electrodes 14 to create a cell necrosis zone 13' of the desired volume. Because of significant heating of tissue immediately proximal of electrode 14, desiccation of tissue adjacent to electrode 14 may result. When the fluid within the tissue is desiccated, minimal or no electrical current flows through the tissue and heating ceases. This problem can be alleviated by using a lower rate of heating which requires extended treatment periods. Referring now to FIG. 8a, in other embodiments the problem can be solved by coupling a cooling means or cooling device 33' to one or more electrodes 14 and/or treatment site 13. In various embodiments cooling device or means 33' can be a cooling fluid (e.g. chilled saline), a cryogenic fluid (e.g a refrigerant) or a peltier effect device. In one embodiment cooling fluid 33 can be coupled to a fluid delivery device 33' (e.g. a peristaltic or other pump) to facilitate delivery of cooling fluid 33 to electrode 14 and/or tissue site 13. Fluid delivery device 33' may have an integral fluid reservoir 33'.

Figure 9A:
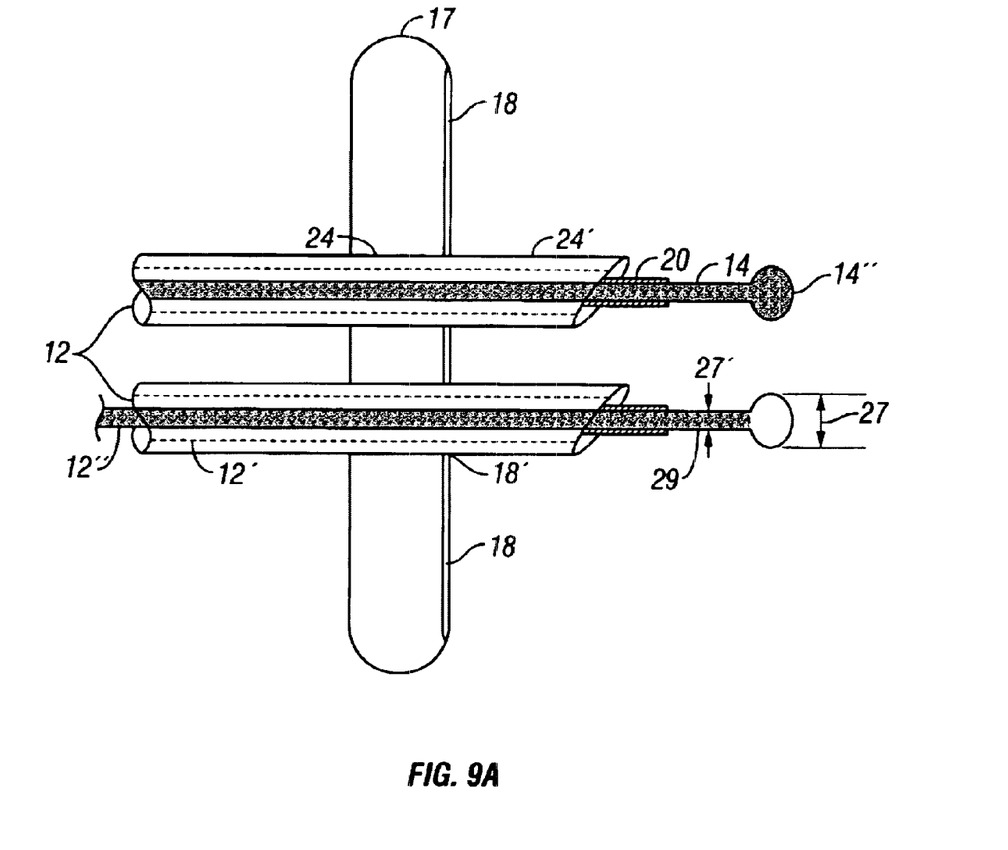
FIG. 9a is a lateral view of distal portion of the apparatus illustrating an embodiment of the apparatus of FIG. 1 that includes tissue piercing stylets.
Figure 9B:
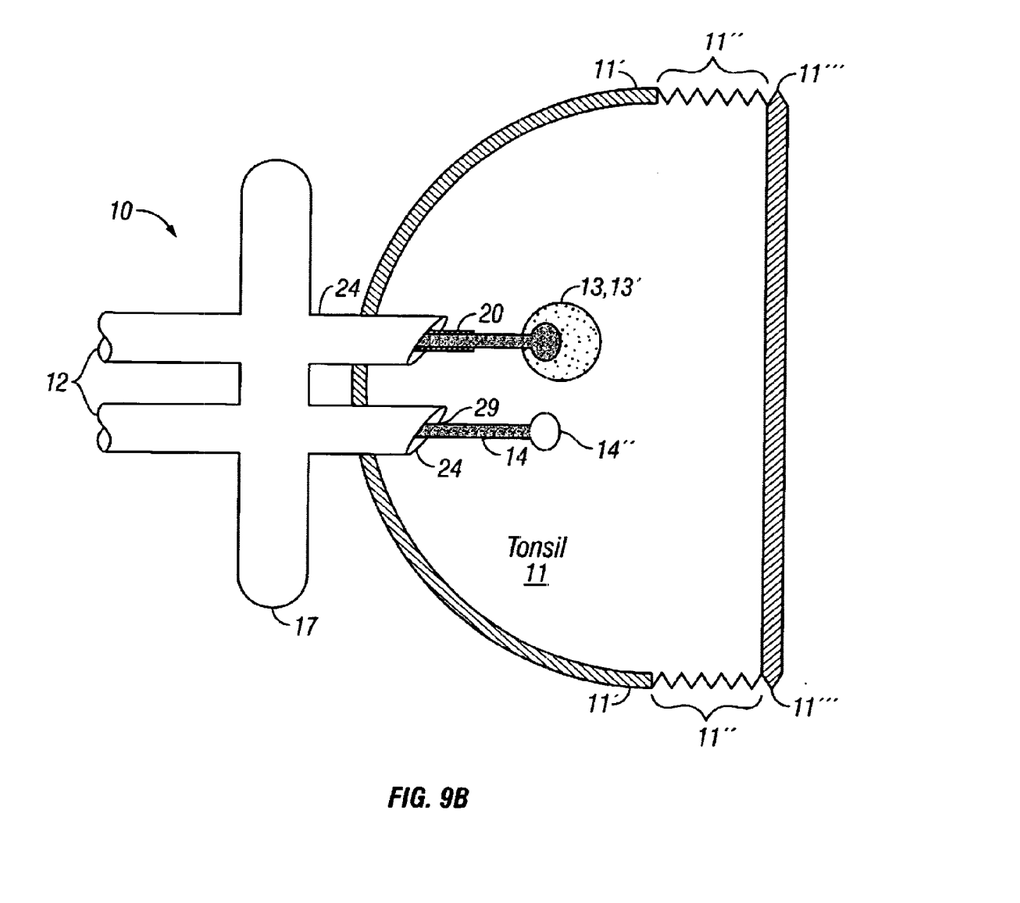
FIG. 9b is an angled lateral view of FIG. 8b illustrating the use of tissue piercing stylets and blunt ball tip electrode to position the electrode in the intratonsil lymphoidstoma while avoiding the back capsule wall of the tonsil.
Figure 9C:
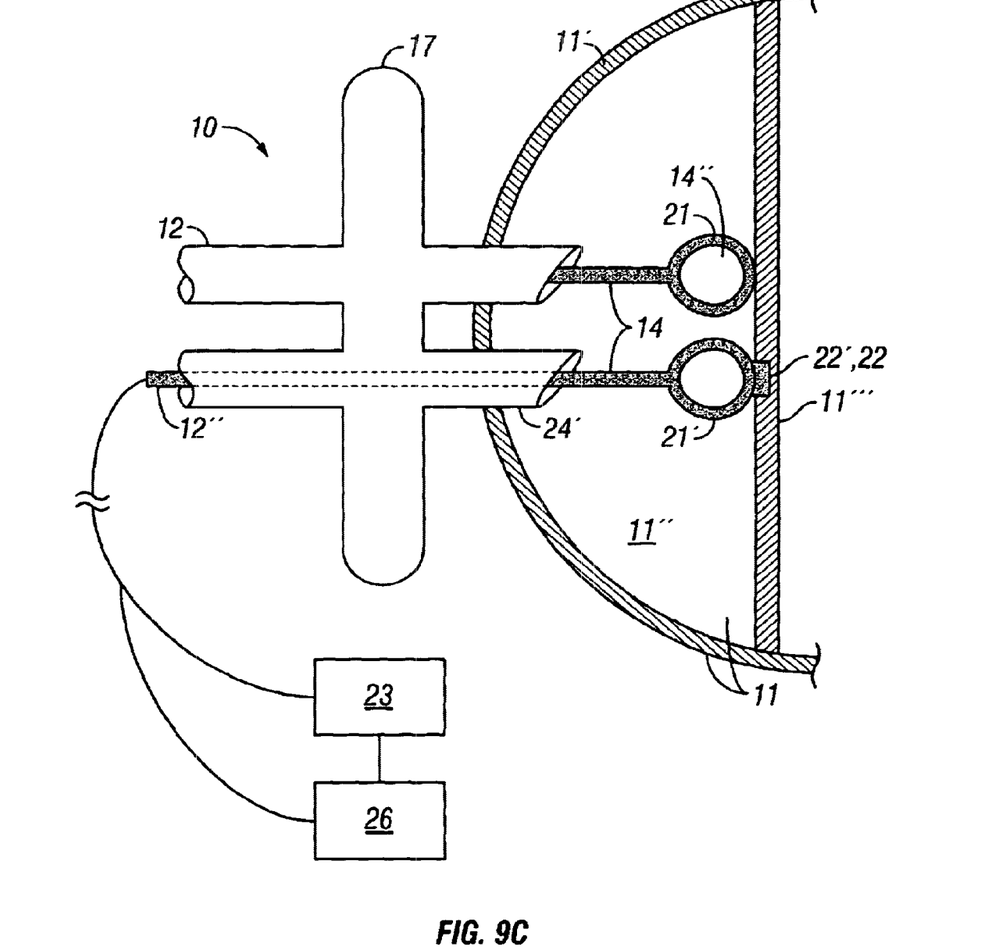
FIG. 9c is lateral view of illustrating the use of an atraumatic/compressible coating on the electrode ball tip along with a force sensor positioned at the electrode tip to provide physician feedback.

Referring now to FIGS. 9a–9c, in various embodiments electrodes 14 may have non-conducting blunt ball tips 14" (also called atraumatic tip 14" or blunt tip 14" or tip 14") which are deployed through stylets 24 into the tonsil lymphoid stroma. In related embodiment, atraumatic tip 14" can have other atraumatic/non piercing geometric shapes including but not limited to cylindrical, circular, oval, spherical and hemispherical; one more of which may have a concave or convex surface 14'". Also blunt tip 14" can have a cross sectional diameter 27 less than a cross sectional diameter 27' of an elongated proximal portion 29 of electrode 14. Limited pressure is applied by the physician to elongated member 12 to bring tip 14" of electrodes 14 into contact with the back capsule wall of the tonsil with minimal or no penetration of the back capsule wall. This configuration provides a more complete exposure of the stromal tissue to RF energy exposure while minimizing injury and damage to the back wall of the tonsil and/or the underlying tissue. In one embodiment tip 14" can be coupled to a force/pressure sensor 22' coupled to a monitoring device 23 to provide the physician feedback on the amount of force/pressure being applied by tip 14" against adjacent tissue and assist him or her in reducing the likelihood of penetration of the back capsule wall. In various embodiments, force/pressure sensor 22' can include a strain gauge, or solid state based (e.g. silicon) pressure/force sensor known in the art. In related embodiments electrodes 14 can be positioned at treatment site 13 in the tonsil 11 or other oral structure without the use of template 17. This can be achieved using electrodes 14 that are either tissue piercing or have fully or partially blunt tip 14". In related embodiments, placement of electrodes 14 without template 17 can be facilitated with the use of sensor 22 including a pressure sensor 22' positioned at tip 14". Placement of electrode 14 can also be facilitated by the use of an endoscopic or fiberoptic viewing device or a medical imaging modality known in the art such as ultrasound, fluoroscopy, MRI or CT scans.

In various embodiments, the blunt ball tips 14" of electrodes 14 can be configured to be atraumatic and/or less likely to puncture tissue through the use of atraumatic soft/compressible coatings 21 such as silicone or other medical elastomers known in the art, as well as foam polymer material known in the art. Coating 21 can be configured to compress to absorb some of the force (including compressive force) applied by tip 14" against the tonsil capsule wall 11'" and reduce the likelihood of penetration of the back capsule wall 11'" of the tonsil 11. In one embodiment coating 21 is configured to have a compressive modulus 21' less than that of capsule wall of the tonsil. In related embodiments, coating 21 can be configured to be electrically and/or thermally insulative and can be the same as or otherwise integral with insulator 20.

Figure 10:
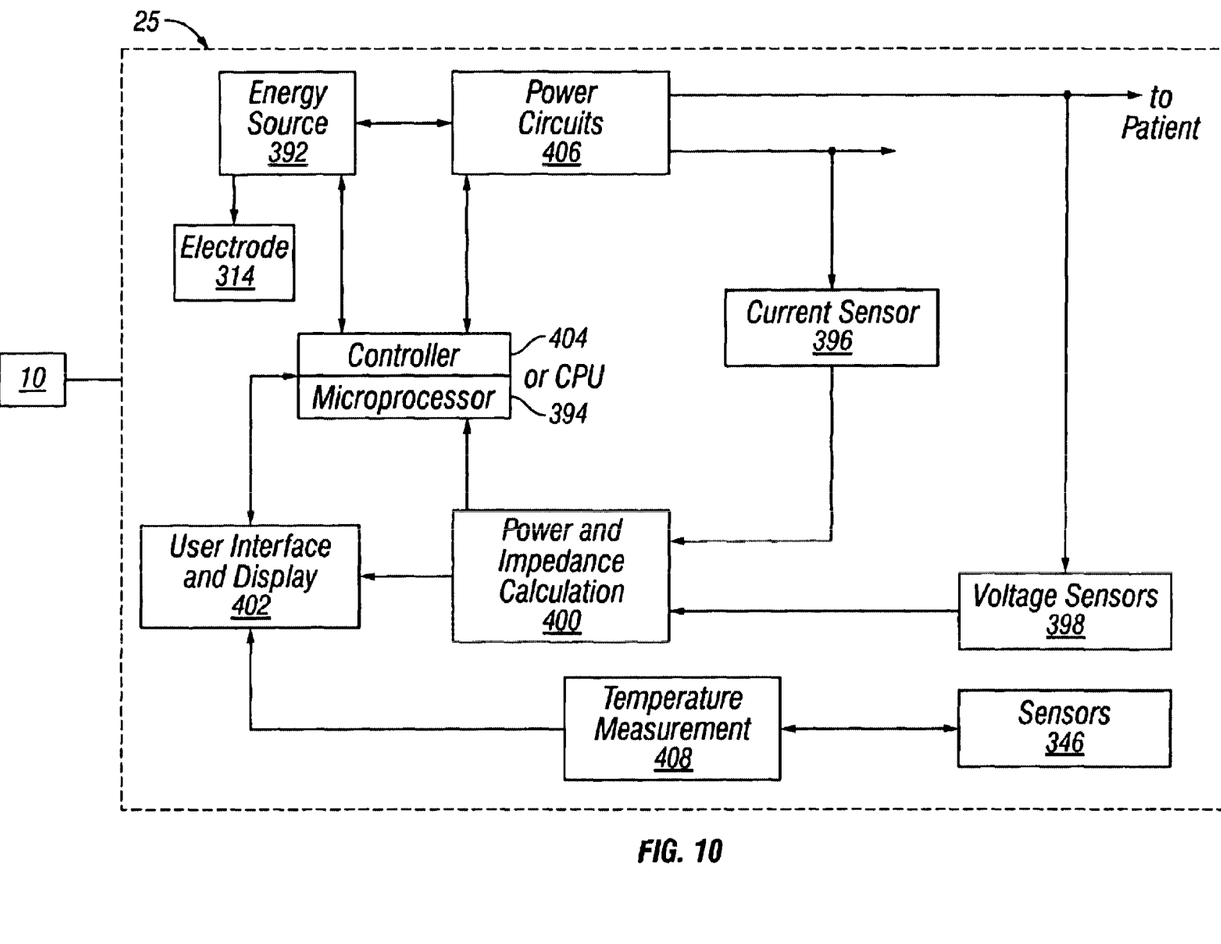
FIG. 10 depicts a block diagram of the feed back control system that can be used with the apparatus as shown in FIG. 3.

Referring now to FIG. 10, in various embodiments cell necrosis apparatus 10 is coupled to an open or closed loop feedback system 25. In one embodiment open or closed loop feedback system 25 couples sensor 346 to energy source 392. In this embodiment, energy delivery device 314 is one or more RF electrodes 314. The temperature of the tissue, or of RF electrode 314 is monitored, and the output power of energy source 392 adjusted accordingly. Additionally, the level of disinfection in the oral cavity can be monitored. The physician can, if desired, override the closed or open loop system. A microprocessor can be included and incorporated in the closed or open loop system to switch power on and off, as well as modulate the power. The closed loop system utilizes a microprocessor 394 to serve as a controller, monitor the temperature, adjust the RF power, analyze at the result, refeed the result, and then modulate the power.

With the use of sensor 346 and the feedback control system a tissue adjacent to RF electrode 314 can be maintained at a desired temperature for a selected period of time without impeding out. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output in an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of energy when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output in an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 402 includes operator controls and a display. Controller 404 can be coupled to imaging systems, including but not limited to ultrasound, CT scanners, X-ray, MRI, mammographic X-ray and the like. Further, direct visualization and tactile imaging can be utilized.

The output of current sensor 396 and voltage sensor 398 is used by controller 404 to maintain a selected power level at RF electrode 314. The amount of RF energy delivered controls the amount of power. A profile of power delivered can be incorporated in controller 404 and a preset amount of energy to be delivered may also be profiled.

Circuitry, software and feedback to controller 404 result in process control, and the maintenance of the selected power setting that is independent of changes in voltage or current, and used to change, (i) the selected power setting, (ii) the duty cycle (on-off time), (iii) bipolar or monopolar energy delivery and (iv) fluid delivery, including flow rate and pressure. These process variables are controlled and varied, while maintaining the desired delivery of power independent of changes in voltage or current, based on temperatures monitored at sensor 346.

Figure 11:
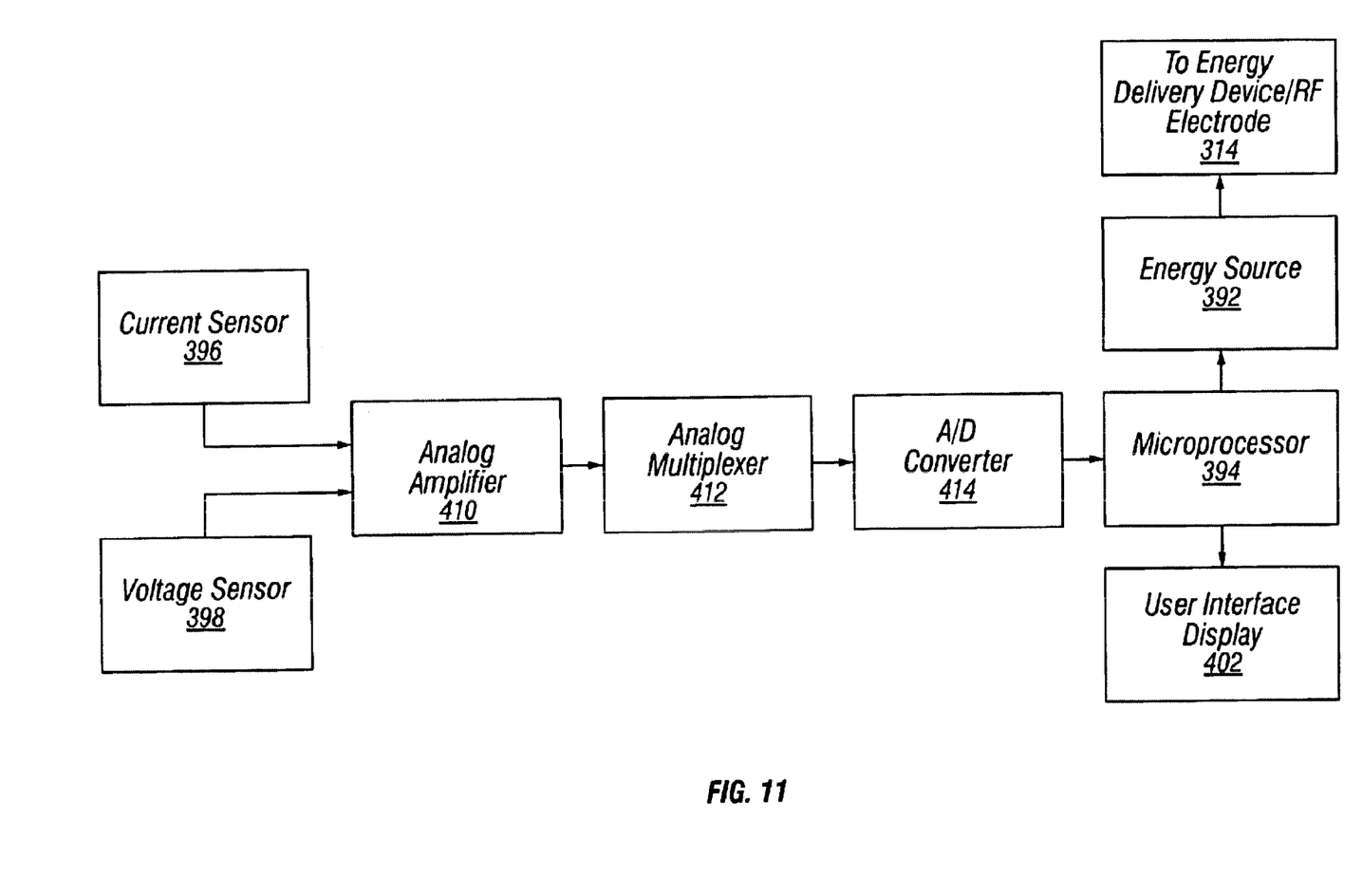
FIG. 11 depicts a block diagram of an analog amplifier, analog multiplexer and microprocessor used with the feedback control system of FIG. 10.

Referring now to FIG. 11, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 with power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 12:
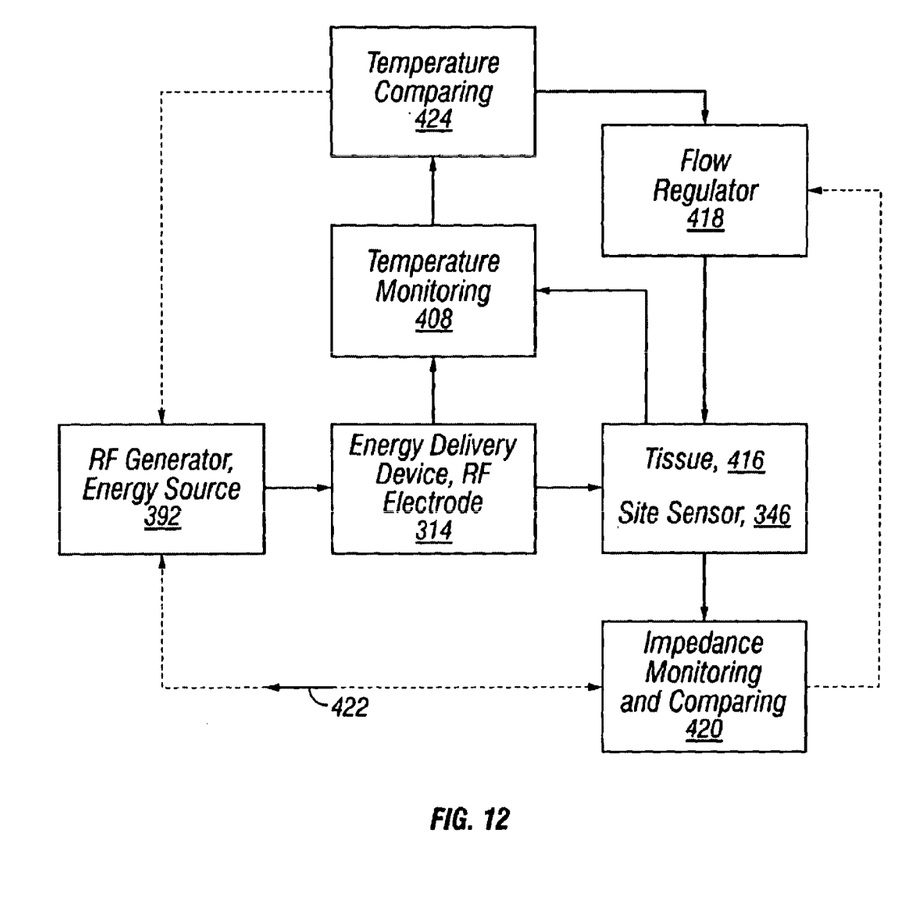
FIG. 12 depicts a block diagram of the operations performed in the feedback control system depicted in FIG. 10.

FIG. 12 illustrates a block diagram of a temperature/impedance feedback system that can be used to control energy delivery and/or fluid flow rate to electrode 314 and/or a tissue site 416 to regulate the temperature of either or both. Energy is delivered to RF electrode 314 by energy source 392, and applied to tissue site 416. A monitor 420 ascertains tissue impedance, based on the energy delivered to tissue, and compares the measured impedance value to a set value. If the measured impedance exceeds the set value, a disabling signal 422 is transmitted to energy source 392, ceasing further delivery of energy to electrode 314. If measured impedance is within acceptable limits, energy continues to be applied to the tissue. During the application of energy, sensor 346 measures the temperature of tissue and/or electrode 314. A comparator 424 receives a signal representative of the measured temperature and compares this value to a pre-set signal representative of the desired temperature. Comparator 424 sends a signal to a flow regulator 418 representing a need for a higher temperature control fluid flow rate, if the tissue temperature is too high, or to maintain the flow rate if the temperature has not exceeded the desired temperature.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A cell necrosis apparatus, comprising:
   an elongated member with a longitudinal and sized to be positionable and maneuverable in an oral cavity;
   a template fixably positioned at a distal portion of the elongated member and including a tissue interface surface;
   a first and a second energy delivery device coupled to the elongated member, the first and second energy delivery devices being laterally offset from the longitudinal axis, each of the first and second energy delivery devices having a tissue piercing distal end.

2. The apparatus of claim 1, wherein the first energy delivery device is a first RF electrode and the second energy delivery device is a second RF electrode.

3. The apparatus of claim 2, further comprising:
   an RF energy source coupled to each of the RF electrodes.

4. The apparatus of claim 2, further comprising:
   a groundpad electrode electrically coupled to the first and second RF electrodes.

5. The apparatus of claim 2, wherein the first and the second RF electrodes are configured to operate in a bipolar mode.

6. The apparatus of claim 2, wherein the first and the second RF electrodes are configured to operate in a monopolar mode.

7. The apparatus of claim 2, further comprising:
   a first insulator sleeve positioned at an exterior surface of the first RF electrode and a second insulator sleeve positioned at an exterior surface of the second RF electrode.

8. The apparatus of claim 2, further comprising:
   a feedback control system coupled to at least one of a sensor or an RF energy source.

9. The apparatus of claim 2, wherein the first RF electrode has a first energy delivery surface and the second RF electrode has a second energy delivery surface.

10. The apparatus of claim 9, wherein each of the first and second RF electrodes has a tissue piercing distal end.

11. The apparatus of claim 9, wherein the first energy delivery surface and the second energy delivery surface each has a size that is sufficient to create cell necrosis in a tonsil intratonsil lymphoid stroma while substantially preserving a tonsil fibrous capsule and a mucosal surface.

12. A tonsil treatment apparatus, comprising:
   an elongated member with a longitudinal axis and sized to be positionable and maneuverable in an oral cavity;
   a template coupled to the elongated member and including a tissue interface surface; and
   a first energy delivery device coupled to the elongated member, the first energy delivery device being laterally offset from the longitudinal axis and having a tissue penetrating distal end that is configured to be advancable relative to the tissue interface surface into a tonsil intratonsil lymphoid stroma.

13. The apparatus of claim 12, wherein the first energy delivery device has an energy delivery surface, wherein a distal end of the first energy delivery device is configured to deliver substantially no energy.

14. The apparatus of claim 12, wherein the tissue interface surface that is substantially non-conductive of electromagnetic energy.

15. The apparatus of claim 12, wherein the first energy delivery device is an RF electrode.

16. The apparatus of claim 12, further comprising:
   a second energy delivery device coupled to the elongated member and laterally offset from the longitudinal axis of the elongated member.

17. The apparatus of claims 16, wherein the distal end of the second energy delivery device has a larger cross-sectional diameter than an elongated section of the first energy delivery device.

18. The apparatus of claim 16, wherein the first energy delivery surface and the second energy delivery surface each have a size that is sufficient to create cell necrosis in the tonsil intratonsil lymphoid stroma while preserving a tonsil fibrous capsule and mucosal surface.

19. A cell necrosis apparatus, comprising:
   an elongated member with a longitudinal axis and sized to be positionable and maneuverable in an oral cavity;
   a template fixably positioned at a distal portion of the elongated member and including a tissue interface surface;
   a first and a second energy delivery device coupled to the elongated member, each of the first and second energy delivery devices having a tissue piercing distal end;
   wherein said template has a lumen for guiding said first energy delivery device and a second lumen for guiding said second energy delivery device, and wherein each lumen has a distal opening located distal to a portion of the template configured to be positioned against an exterior surface of a selected anatomical structure.

20. A cell necrosis apparatus, comprising:
   an elongated member with a longitudinal axis and sized to be positionable and maneuverable in an oral cavity;
   a template fixably positioned at a distal portion of the elongated member, wherein a portion of the template is positionable to engage an exterior surface of a selected anatomical structure while another portion of the template is positionable below said exterior surface;
   a first and a second energy delivery device coupled to the elongated member, each of the first and second energy delivery devices having a tissue piercing distal end.

21. A cell necrosis apparatus, comprising:
   an elongated member with a longitudinal axis and sized to be positionable and maneuverable in an oral cavity;
   a template fixably positioned at a distal portion of the elongated member and including a tissue interface surface extending radially outward beyond an elongate portion of the elongate member;
   a first and a second energy delivery device coupled to the elongated member, each of the first and second energy delivery devices having a tissue piercing distal end.

22. A cell necrosis apparatus, comprising:
   an elongated member with a longitudinal axis and sized to be positionable and maneuverable in an oral cavity;
   a template fixably positioned at a distal portion of the elongated member including a curved tissue interface surface;
   a first and a second energy delivery device coupled to the elongated member, each of the first and second energy delivery devices having a tissue piercing distal end.

* * * * *